United States Patent [19]

Liang et al.

[11] Patent Number: 4,989,253

[45] Date of Patent: Jan. 29, 1991

[54] VOICE ACTIVATED MICROSCOPE

[75] Inventors: Marc D. Liang; Krishna Narayanan, both of Pittsburgh; John L. Kurtz, Indiana, all of Pa.

[73] Assignee: The Montefiore Hospital Association of Western Pennsylvania, Pittsburgh, Pa.

[21] Appl. No.: 182,225

[22] Filed: Apr. 15, 1988

[51] Int. Cl.⁵ .............................................. H03G 3/20
[52] U.S. Cl. .................................... 381/110; 367/198; 128/897; 901/1; 901/49
[58] Field of Search ............................ 381/110, 41–43; 901/1, 49; 128/4, 6, 303.1, 897; 604/20; 364/513, 513.5; 367/198

[56] References Cited

U.S. PATENT DOCUMENTS

| | | | |
|---|---|---|---|
| 4,012,112 | 3/1977 | Masterson | 350/531 |
| 4,158,750 | 6/1979 | Sakoe et al. | 381/43 |
| 4,374,618 | 2/1983 | Howard | 355/50 |
| 4,450,546 | 5/1984 | Kanny | 369/24 |
| 4,472,617 | 9/1984 | Ueda et al. | 381/43 |
| 4,473,074 | 9/1984 | Vassiliadis | 128/303.1 |
| 4,538,608 | 9/1985 | L'Esperance, Jr. | 364/413.26 |
| 4,581,647 | 4/1986 | Vye | 358/209 |
| 4,604,016 | 8/1986 | Joyce | 414/5 |
| 4,605,080 | 8/1986 | Lemelson | 364/567 |
| 4,633,499 | 12/1986 | Nishioka et al. | 381/43 |
| 4,641,292 | 2/1987 | Tunnell et al. | 381/110 |
| 4,757,541 | 7/1988 | Beadles | 381/43 |
| 4,776,016 | 10/1988 | Hansen | 381/42 |

OTHER PUBLICATIONS

Application for Ben Franklin Partnership Challenge Grant, Marc D. Liang et al, Mar. 27, 1987 (26 pages).

*Primary Examiner*—Forester W. Isen
*Attorney, Agent, or Firm*—Harry B. Keck

[57] ABSTRACT

A microscope has a voice activated control system which permits precise location of the microscope and precise focusing by means of voice commands uttered by the microscope operator. When the microscope is in a movement mode, the movement is terminated by any sound exceeding a pre-established acoustic threshold level. Any microscope location can be identified and appropriate data is stored in a memory drive to permit the microscope to return to an identified location with a single voice command. The microscope is combined with a screen monitor and/or an acoustic speaker to provide visible and/or acoustic responses from the control system. The system is practical for retrofitting existing remotely controllable microscopes.

10 Claims, 2 Drawing Sheets

VOICE ACTIVATED MICROSCOPE

BACKGROUND OF THE INVENTION

1. Field of the Invention

This invention relates to a microscope which can be positioned and focused in response to voice commands from the microscope user.

2. Description of the Prior Art

There are many applications for microscopes which are positionable within a small field of movement, particularly in the practice of microsurgery. There are available surgical microscopes including a fixed base with a cantilevered support for a microscope a supporting structure for and its focusing mechanism. Such available surgical operating microscopes can be positioned within a limited field of movement by control motors which position the microscope mount at selected locations within the limited field of movement. The control motors can be operated by pressing appropriate buttons or foot pedals. Existing microscopes respond by moving in a vertical direction, i.e., up and down. Additionally the microscope can be caused to tilt about one or more axes by means of appropriate mountings, e.g., gimbel joints, control motors. Further, the microscope focal length can be established by means of control motors which increase or decrease the space between ocular and objective lenses.

In another technology discipline, isolated word recognition systems have been developed to recognize and discriminate isolated words which have been trained into the systems. Such speech recognition devices have been summarized by D. Raj Reddy in an article entitled "Speech Recognition by Machine: A Review" published in the Proceedings of the IEEE, April 1976, page 501-531.

At the present time, microsurgeons control the position and focus of surgical operating microscopes (1) by manual adjustment of the microscope, (2) by manually pressing buttons on control boxes and (3) by pressing pedals to position the surgical operating microscope where needed, when needed and with the appropriate focal length. In the course of most microsurgical procedures, the operating surgeon has both hands fully occupied with surgical instruments and is unable to make manual fine adjustments of the surgical operating micrscope in the middle of a surgical routine, e.g., completing a suture, exposing a tissue, etc. It is impractical to have other person in the operatory attempting to make adjustments to the surgical operating microscope.

Accordingly there is a need for a surgical operating microscope which can be positioned and focused in response to speech commands from the microscope operator. There is also a need for programmable microscope movements, and a need for instantaneous voice-commanded stop functions and a need for the control system to speak back or to display to the operator an indication of which function is active in the microscope. There is a need to provide equipment which can be retrofitted to existing, costly controllable-position microscopes to achieve these objectives in existing equipment.

STATEMENT OF THE PRESENT INVENTION

The present invention provides a controllable surgical operating microscope which can be positioned and have its focal length established in response to speech commands provided by the microscope operator. The invention provides programmable microscope movements, an instantaneous noise-commanded stop-function and means to speak back to or to display to the operator that function which is active in the microscope. The invention also provides means for the microscope to return to a previously identified location on a voice command.

According to the present invention, a surgical operating microscope is provided which has a base and, cantilevered from the base, has a microscope supporting structure which can be position through appropriate control devices at any desired location within a defined spatial field, that is, can be moved in X-Y-Z directions. Appropriate control motors such as servo motors control movement in at least two perpendicular linear loci. A microscope is positioned within the microscope mount and is provided with appropriate control motors such as servo motors to adjust the focal length. The inclination of the microscope within the microscope supporting structure may be manually adjusted at the start of a procedure for the individual operator. All of the control motors required to position the microscope supporting structure and to establish the focal length of the microscope are under the control of computer means which responds to isolated-word recognition devices, of which there are many available as set forth in the article by D. Raj Reddy, supra.

In the present invention, a control system include (a) an isolated-word recognition device which recognizes a limited number of speech commands and provides a unique electrical signal or a unique computer word in response to each recognized speech command, and (b) a computer to control movements of selected control motors and to record the direction an distance of movements in order to:

(1) provide programmable control to return the microscope to previous locations which are recorded in the computer memory;

(2) to move the microscope through established search patterns; and (3) to advance the microscope movement (and hence the microscope) to selected locations by voice commands of the operator.

The control motors may be analog electric motors or digital stepping motors.

The control system provides sequential mode recognition to permit movement and speed control for selected controlled movements. In one embodiment, the control system includes memory means for recording control signals corresponding to a desired location and focal length for the surgical operating microscope.

In another embodiment, the voice activated surgical operating microscope provides a means for generating a STOP signal for all movements of the microscope. The STOP signal is a response to any sound which is detected during a movement mode of the microscope.

The objects and advantages of the present invention will become apparent int he following detailed description by reference to the accompanying drawings.

DESCRIPTION OF THE PREFERRED EMBODIMENTS

Figure 1:
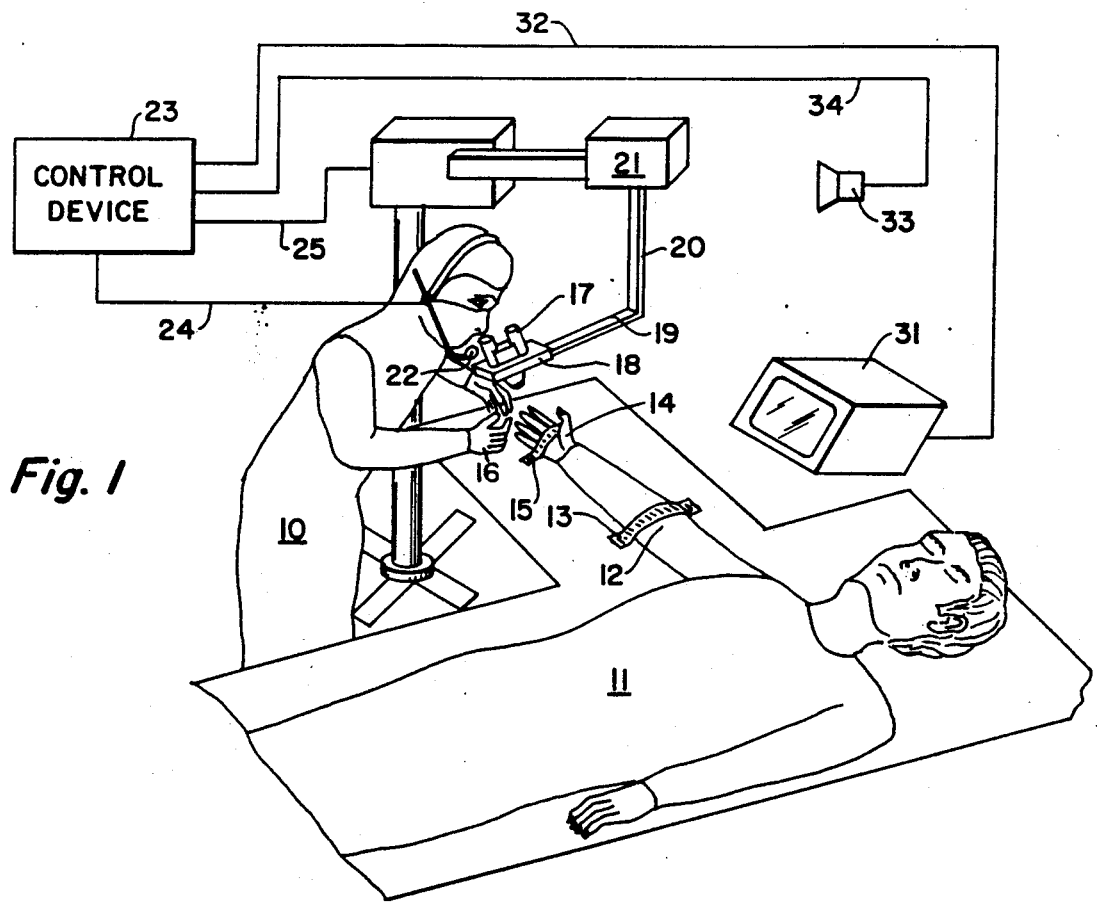
FIG. 1 is a perspective schematic illustration of a microsurgeon conducting a surgical procedure on an anaesthetized hand of a patient, using a voice activated surgical operating microscope of the present invention.

A typical microsurgical procedure is illustrated in FIG. 1 wherein a microsurgeon 10 is performing microsurgery for a patient 11 whose right arm 12 is secured by a restraint 13 and whose anaesthetized hand 14 is secured by a restraint 15. The microsurgeon 10 is shown to be using both of his hands 16 to carry out the procedure.

A microscope 17 is secured in a microscope supporting structure 18 which is cantilevered through structural support members 19, 20 to a rigid mounting box 21, which in a preferred embodiment contains servo devices to position structural support members 19,20.

An audio microphone 22 is provided for the microsurgeon 10 to communicate instructions to the control system of the present invention whereby:

(a) the microscope supporting structure 18 may be moved in selected directions by means of appropriate adjustment of the structural support members 19,20;

(b) the focal length of the microscope 17 may be adjusted; and, in some embodiments, (c) the inclination of the microscope 17 with respect to the microscope supporting structure 18 may be adjusted.

As a consequence of the present invention, the microsurgeon 10 can continuously view the patient's hand 14 through the microscope 17 while having both hands 16 available for efficient, uninterrupted completion of the surgical procedure. A typical procedure of the type illustrated in FIG. 1 is an anastomosis of a vein or an artery in the patient's hand 14.

Figure 2:
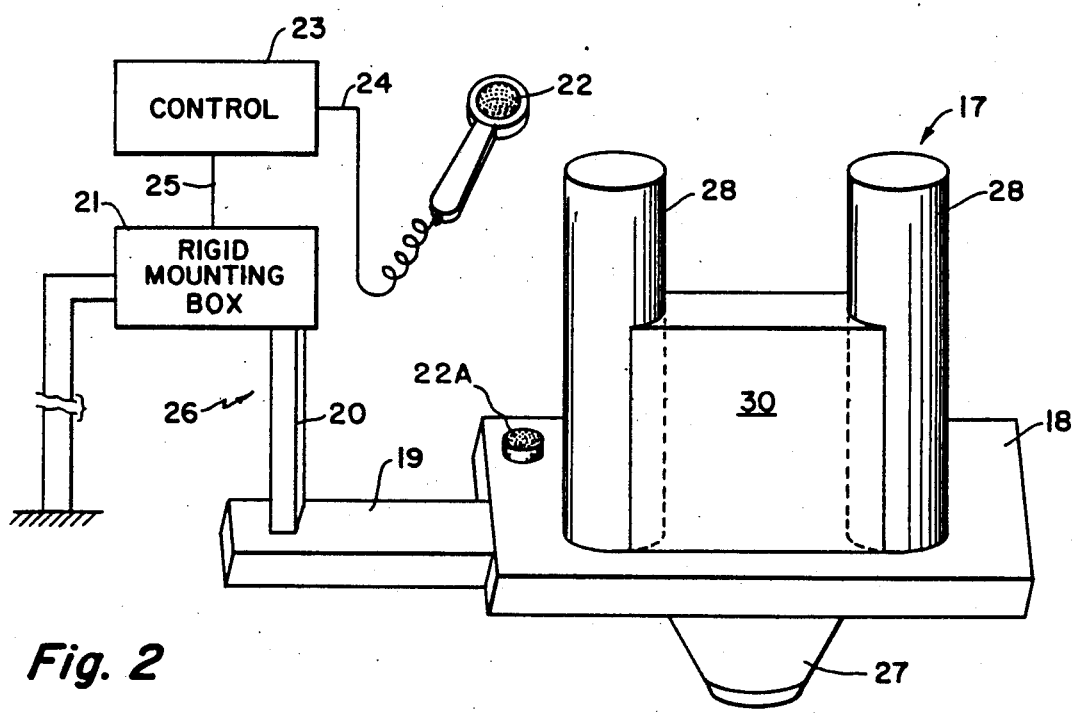
FIG. 2 is a schematic representation of the surgical operating microscope of this invention.

Elements related to this invention are illustrated in FIG. 2 which includes the microscope supporting structure 18, the microscope 17, the structural supporting members 19, 20, the rigid mounting box 21 and the operator's audio microphone 22 which is connected to a control device 23 by means of a conductor cable 24. Alternatively the acoustic microphone 22 may have radio transmission capability and the control device 23 may have a radio receiving capability so that the conductor cable 24 can be eliminated and radio communication can be substituted. As a further alternative, the microphone 22A may be secured to the microscope 17 or to the microscope supporting structure 18.

The control device 23 is shown to be connected to the rigid mounting box 21 by means of a conductor 25. Similarly the control device 23 may generate radio signals which are transmitted to a radio receiver within the rigid mounting box 21.

The control device 23 comprises a computer as the principal component having as its peripheral devices an isolated-word recognition device, interface hardware for a microscope movement activator, and a speaker 33 (FIG. 1) and an information display monitor 31 (FIG. 1).

Figure 3:
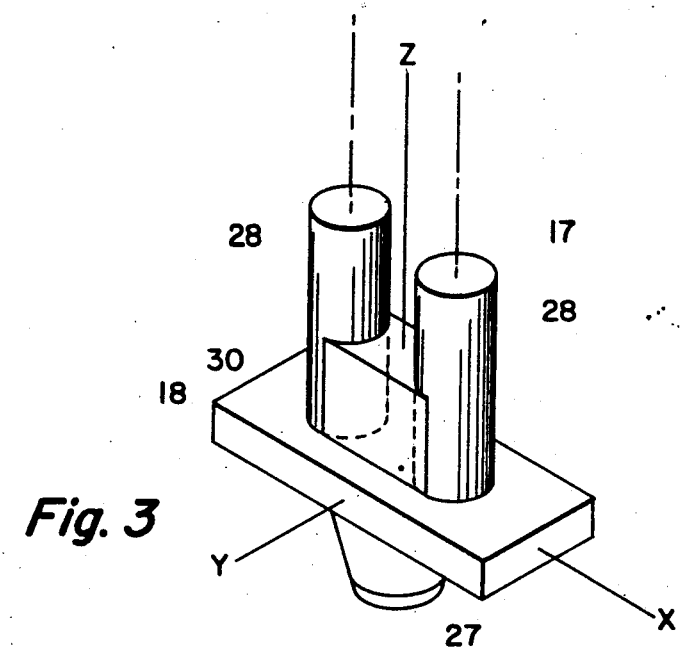
FIG. 3 is a perspective sketch of a typical microscope illustrating movements.

Mounting system 26 (rigid mounting box 21 and structural support members 19, 20) contains motor-operated first means (the construction of which forms no part of the present invention), which extend, rotate and retract the structural support members 19, 20 in order to position the microscope supporting structure 18 as desired. Movements of the microscope supporting structure 18 may occur as indicated graphically in FIG. 3 in the X direction, the Y direction or the Z direction corresponding to left-right, forward-back, up-down. Excellent results can be achieved with controlled movement only in the X-direction and the Y-direction. The operator can manually position the microscope at an appropriate elevation so that no Z-direction movement is needed.

The microscope 17 has an objective lens 27 and binocular lenses 28. The microscope 17 has two parallel longitudinal axes 29 which can be maintained at a fixed inclination with respect to the microscope supporting structure 18. The microscope may be pivotally joined to the microscope supporting structure 18 to permit adjustment of the angle of inclination between the longitudinal axes 29 and the microscope supporting structure 18. In a preferred embodiment, the microscope 17 may be securely mounted with respect to the microscope supporting structure 18 and the inclination of the microscope supporting structure 18 may be adjusted by appropriate mechanical movements of the structural members 19, 20, i.e., by rotation about the X-axis of FIG. 3.

The focal length adjusting device 30 is a motor-operated second means, interposed between the microscope supporting structure 18 and the microscope 17 to permit lengthwise adjustment of the binocular lenses 29 with consequent adjustment of the focal length of the microscope 17. A worm gear and toothed rail device may be employed to achieve lengthwise extension and contraction of the binocular lenses 28.

All of the movements of the microscope, thus far described, can be accomplished by a remote operating control device having buttons or pedals to control the speed and nature of each of the microscope movements.

In operation, the acoustical sounds (command words) introduced at the audio microphone 22 are delivered as audio-electrical signals through the conductor 24 to the control device 23 which delivers a corresponding actuating electrical signal through the conductor 25 to the rigid mounting box 21. The actuating electrical signals operate the various motors in the microscope supporting structure 18, the structural support members 19, 20 and in the rigid mounting box 21. When the microscope 17 or supporting structure 18 is in a movement mode, the audio-electric signal bypasses the isolated-word recognition software and delivers a digital signal directly to the motor control software so that any acoustic input will halt the existing movement mode instantaneously.

Initially the microscope supporting structure 18 is positioned in the general region of operation, the structural support members 19, 20 are approximately midway within the range of movements for the microscope mount 18 in the X-Y directions and the Z-direction, if controllable. Thereafter the operator causes the desired movement of the microscope mount 18 by appropriate voice commands, for example, "LEFT", which is detected in the control device 23. The movement will proceed to the left along the X-axis at a pre-established velocity unless the operator precedes the direction command with an audible instruction, "ZOOM", which is identified int he control device 23. A corresponding actuating electrical signal is delivered through the conductor 25 to the rigid mounting box 21 to move at an increased speed. The movement will continue until the microscope mount 18 has reached the end of the available focus of movement or until the control device 23 receives a STOP command which is delivered orally through the audio microphone 22 and the conductor 24.

The operator can thereafter provide another signal sequence, e.g., DOWN, UP, ZOOM-RIGHT, ZOOM-UP, etc., which will cause a movement of the microscope mount 18 until an appropriate STOP signal is received and carried out. Thereafter the operator can observe through the binocular lenses 28 and provide a vocal command to "FOCUS DOWN" which will be recognized by the isolated-word recognition device and which will result in an appropriate electrical signal from the control device 23 to the rigid mounting box 21 through conductor 25. The conductor 25 continues (not seen in FIG. 2) through the structural support members 20, 19 and delivers an electrical signal to the focal length adjusting device 30 causing the tubes of the microscope 17 to change length with a corresponding change in the focal length of the microscope 17 until the operator delivers an audible a "STOP" command when the object of micrscopic observation is in proper focus.

It is desirable for the surgeon 10 to be aware of the vocal commands which have been received by the control device 23. Accordingly it is desirable as shown in FIG. 1 to have a visible screen monitor 31 connected through a cable 32 to the control device 23. In a preferred embodiment, the television screen monitor 31 will display the operator's commands which have been received and executed. Thus if the operator 10 commands "ZOOM LEFT", the phrase "ZOOM LEFT" will appear on the visible screen monitor 31. The visible screen monitor 31 may provide an audible indication, such as a beep, if the control device 23 was unable to discriminate the operator's command. If desired, the monitor screen image can be projected with a beamsplitter directly to an appropriately-equipped microscope 17 where the image will appear in the viewing field of the microscope 17.

A further desirable feature is an audio-speaker 33 connected to the control device 23 through cables 34, 32. The audio-speaker 33 may be connected to a voice synthesizer within the control device 23 which will provide an audible response to indicate which message the control device 23 has received and executed. Thus if the operator 10 issues a vocal command "UP", the control device 23 will recognize the instruction and will repeat the word "UP" at the audio-speaker 33. If the control device 23 did not recognize the word "UP", the audio-speaker 33 will remain silent or will articulate the command word which was received by the control device 23. Alternatively, an acoustic "beeping" means may generate audible sounds when a spoken word is not recognized by the isolated word identification software to a desired degree of confidence.

OPERATION

The present invention has a training regiment for each operator in order to provide recognition of the unique speech patterns of each operator. Each word command in the machine vocabulary is trained into the system's memory by each operator at least twice. In a preferred embodiment, the individual word commands in the system vocabulary appear on the visible screen monitor 31, or are uttered by the voice synthesizer through the speaker 33. This constitutes a request by interactive software associated with the computer means for utterance of each pre-established word command. The operator 10 speaks each word command into the microphone 22. The voice pattern of the operator 10 is retained in memory within the control device 23. After the operator 10 has trained his unique vocal commands into the system, it may not be necessary to repeat the training for each reuse of the system by the operator; instead, the prior memory may be called up for the operator 10. If, during the training regimen, the operator 10 utters a particular word command differently, the word recognition program will require further repetition of the word command until at least two closely matching voice patterns are received for each word command in the vocabulary.

A commercially available isolated-word recognition program can be purchased under the trademark VOICEMASTER (COVOX, Inc.) available for use with a Commodore 64 (TM) computer. The purpose of the training regiment is to assure that the isolated-word recognition program will identify the words of the operator 10 and carry out the intended functions.

The isolated-word recognition devices are "templates" —which correspond to each programmed utterance. In the present invention, the software preferably is designed to require at least two, preferably three, such templates for each utterance. The audio electrical signal is evaluated by its comparison to each of the command word templates in the memory. The templates with the highest "score" indicate the command word which will be identified by the word-recognition device.

The proposed vocabulary for the microscope is intentionally limited for ease of use. A proposed vocabulary consists of eight words:

| UP | DOWN |
| LEFT | RIGHT |
| FORWARD | BACK |
| ZOOM | FOCUS |

These eight words will be employed by the operator in 14 different combinations:

| UP | ZOOM UP |
| DOWN | ZOOM DOWN |
| LEFT | ZOOM LEFT |
| RIGHT | ZOOM RIGHT |
| FORWARD | ZOOM FORWARD |
| BACK | ZOOM BACK |
| FOCUS UP | |
| FOCUS DOWN | |

Additional commands can be employed where the microscope has location memory features:

| POINT | RETURN |
| ONE, TWO, THREE, FOUR, FIVE ... etc. | |

During the operation of the device, the operator initiates movement of the microscope mount by any of the following expressions: UP, DOWN, LEFT, RIGHT, FORWARD, BACK, ZOOM UP, ZOOM DOWN, ZOOM LEFT, ZOOM RIGHT, ZOOM FORWARD, ZOOM BACK. The direction of the movement is with respect to the operator 10 (FIG. 1). Each of these instructions will cause the microscope mount 18 to move in the indicated direction at a normal speed or at an increased (ZOOM) speed.

When the microscope supporting structure 18 has moved to the desired position, the operator commands STOP or any other word. The control device 23 is programmed to cause immediate stoppage of the existing movement mode in response to the next sound received by the control device 23.

When the microscope supporting structure 18 is in the desired location, the operator can adjust the focus of the microscope 17 with the commands FOCUS UP or FOCUS DOWN followed by the STOP command when the desired field of observation becomes clear.

Within the control device 23, a timer means (e.g., a clock) maintains a record of the movements in each of the available directions (UP, DOWN, LEFT, RIGHT, FORWARD, BACK) from the initial location. When the operator determines an appropriate position, the operator can instruct the control device with the phrase POINT followed by a number, for example, POINT-ONE. The control device 23 will record the distances from the initial location in each movement direction. Thereafter, when the phrase RETURN-ONE is spoken, the control means will restore the microscope to the location previously identified by the operator as POINT 1. A number of additional memory locations can be available. Five such locations seems to be a realistic maximum. Similarly the distances moved by the FOCUS UP, FOCUS DOWN operating device from the initial position can be recorded in the memory device corresponding to the POINT-(NUMBER) indication so that the user may return to prior locations and the microscope will be properly positioned and focused for each procedure.

If the available microscope has controllable movements only in the X and Y directions at a single movement speed and has no controllable focus apparatus, the vocabulary can be reduced to:
LEFT
RIGHT
which will provide voice control of the available movements. The timing regimen can be shortened correspondingly.

Figure 4:
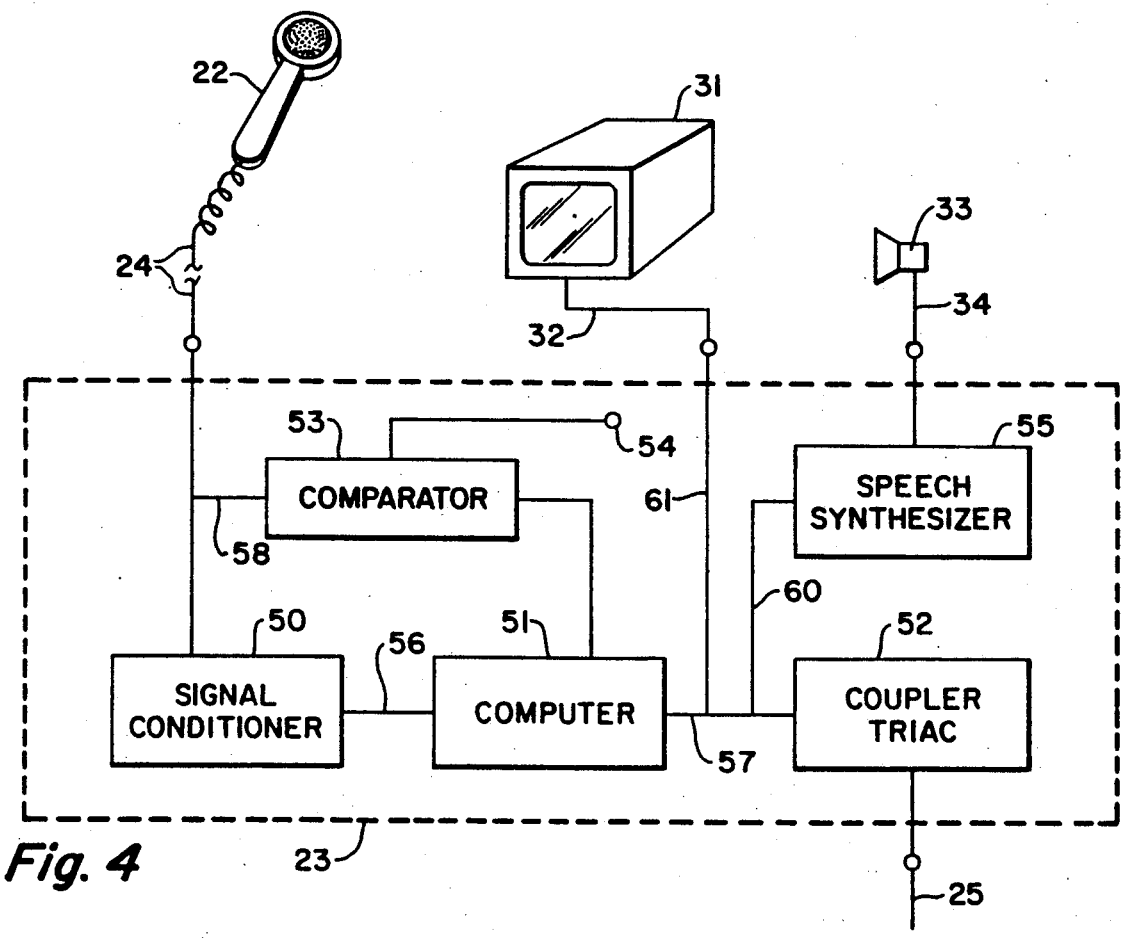
FIG. 4 is a schematic illustration of appropriate control circuitry employed int he several embodiments of this invention.

Referring to FIG. 4, the control device 23 is indicated as a broken-line box. The control device 23 receives an audio electric signal from a conductor 24 and delivers actuating electrical signals through a conductor 25 to control the movement of the servo devices which cause movements of the microscope mount and the microscope focal lengths. The conductors 32, 34 deliver operating electrical signals to a visible screen monitor 31 and an acoustic speaker 33.

Within the control device 23, in the preferred embodiment, there is a signal conditioner 50, a computer 51, a coupler triac 52, a comparator 53, source of fixed d.c. voltage 54 and a speech synthesizer 55. The coupler triac is a preferred output signal generator which generates actuating electrical signals. In the preferred embodiment, the control device 23 is software-controlled by the computer 51.

The signal conditioner 50 receives the audio-electrical signal from the conductor 24 and identifies the words to create an identified electrical signal delivered through a conductor 56 to the computer 51. A typical signal conditioner 50 is commercially available under the trade name COVOX VOICE MASTER.

NOTE: The COVOX VOICE MASTER provides both hardware and software but is compatible with the software in the computer 51.

The computer 51 develops an appropriate operating electrical signal and delivers that operating electrical signal through a conductor 57 to the coupler triac 52 which generates and delivers corresponding actuating electrical signals to the servo devices in the rigid mounting box 21 to effect the intended movement of the microscope supporting structure 18 and microscope 17. The computer 51 includes counter-means for recording the duration and speed of each movement mode to develop a memory for each SET POINT position of the supporting structure 18 and microscope 17. The computer 51 also includes interactive software to direct the training regimen for each user.

The comparator 53 is a preferred means for the STOP function of this invention. The incoming audio-electric signal from the conductor 24 is delivered to the comparator 53 by conductor 58. The voltage of the audio-electric signal from the conductor 58 is compared with a threshold voltage from the d.c. voltage source 54. The output signal from the comparator 53 is delivered to a conductor 59 directly to the computer 51 as a digital signal —that is, a first signal or a second signal, digitally represented as a "one" or a "zero". When the "one" signal is received by the computer 51, the existing movement mode is instantly terminated; when the "zero" signal is received, the movement may continue uninterrupted. If there is no existing movement, the computer is unaffected. The comparator 53 by-passes the signal conditioner 50 and thereby develops an instantaneous response to any sound above a pre-established threshold which can be set at the d.c. voltage source 54. The instantaneous response to any sound exceeding the pre-established threshold provides a fail-safe feature for the microscope movement control system.

Alternatively a digital signal circuit (not shown) may provide the STOP function of the system. The described analog circuit will function instantaneously whereas the digital signal circuit can halt movement in about one millisecond.

An operating electrical signal for the conductor 57 is delivered through a conductor 60 to the speech synthesizer 55 which generates an audio speech signal corresponding to that which has been identified by the signal conditioner 50. For example, if the operator commands ZOOM-UP, then the speech synthesizer 55 will create the audio speech signal ZOOM-UP which the user can hear from the audio speaker 33 to verify that the correct motion has been activated. The wrong message or no message from the audio speaker 33 indicates that the system misunderstood the command or did not receive the command or is otherwise malfunctioning. Alternatively the operating electrical signal from the conductor 57 can be directed to the display monitor 31 through a conductor 61 so that the active command will be visibly displayed for the user's guidance, e.g., the words ZOOM-UP will appear on the visible screen monitor.

Developing Speech Vocabulary

In a preferred embodiment of the invention, the computer 51 includes interactive software to enable each individual operator to develop unique voice recognition patterns for the control system. The individual operator will be requested either audibly through the audio speaker 33 or visibly from the visible screen monitor 31 or both to speak into the audio microphone 22 each of the word commands in the control system vocabulary. Each of the word commands will be repeated and will require an audible response from the operator until vocabulary memory means within the computer 51 has at least two speech patterns which are identifiable with the word command. At this training stage, substitute word commands may be employed which are the equivalent of the normal and customary word commands. For example, the word UP may be expressed by a foreign language operator by some other expression which is the foreign language equivalent of UP. The computer 51 thereafter will recognize that term as the equivalent of the UP voice command for that foreign language operator. Thus the computer 51 has a memory which can identify the vocabulary word commands or their equivalents for each of the intended movement modes. The vocabulary training regimen continues until each of the vocabulary word commands has been expressed and accepted at least twice by the computer memory.

In extended surgical procedures, where operators alternate their surgical functions, the same surgical microscope may be employed alternately by different operators. If each operator has trained his unique vocabulary into the vocabulary memory, the computer 51 can employ the pre-established vocabulary memory of each active operator.

Established Search Patterns

The control device 23 may be programmed to move the microscope supporting structure 18 through pre-established search patterns, e.g., left-to-right; up-to-down; forward-to-back. Another search program advances the microscope mount from the maximum UP-LEFT-FORWARD position to the maximum DOWN-RIGHT-BACK position to provide the operator with an appreciation of the range of available movement. A further pre-established program is to position the microscope supporting structure 18 at the mid-range of the LEFT-RIGHT movement, the UP-DOWN movement and the FORWARD-BACK movement for initiating a particular surgical procedure.

We claim:

1. In an optical microscope having supporting structure and motor operated first means to position said supporting structure at selected locations, the improvement comprising:
   sound detection means for converting acoustic energy into audio-electrical signals;
   control means including:
   isolated-word recognition means for identifying pre-established word commands from said audio-electrical signals and for generating corresponding identified electrical signals;
   computer means for generating operating electrical signals corresponding to said identified electrical signals;
   output signal generator means, responsive to said operating electrical signals to deliver actuating electrical signals to said motor operated first means to actuate said motor operated first means;
   whereby word commands corresponding to said pre-established word commands, applied to said sound detection means will result in pre-established movements of said supporting structure.

2. The optical microscope of claim 1 wherein said pre-established word commands include six words which can be identified by said isolated-word recognition means including:
   UP (or its equivalent); DOWN (or its equivalent); LEFT (or its equivalent); RIGHT (or its equivalent); FORWARD (or its equivalent); and BACK (or its equivalent);
   and wherein said activating electrical signals actuate said motor-operated first means to move said microscope supporting structure respectively UP, DOWN, LEFT, RIGHT, FORWARD and BACK with reference to the microscope user.

3. The optical microscope of claim 1 wherein said computer means includes first memory means for recording pre-established voice commands form an intended operator of said optical microscope.

4. The optical microscope of claim 1 including:
   computer counter means for measuring the direction and distance of each movement of said microscope supporting structure from an initial location;
   computer memory means to record the instantaneous summation of said counter means at an identified instant in response to a pre-established word command applied to said sound detection means; and
   means for restoring said microscope supporting structure to the position of said microscope mount at said instant.

5. In an optical microscope of claim 1, stop means for stopping any movement of the said microscope mount when any audio-electrical signal is delivered to said control means having an amplitude which exceeds a pre-established threshold amplitude while said microscope supporting structure is in motion.

6. The optical microscope of claim 5 wherein the stop means includes a voltage comparator which compares the voltage of said audio-electrical signal to a pre-established d.c. voltage and delivers to said computer means a first signal when said audio-electrical signal is less than said threshold voltage and delivers to said computer means a second signal when said audio-electrical signal is equal to or greater than said threshold voltage.

7. In an optical microscope having supporting structure, motor operated first means to position said supporting structure at selected locations and motor operated second means to establish the focal length of said microscope, the improvement comprising:
   sound detection means for converting acoustic energy into audio-electrical signals;
   control means including:
   isolated word recognition means for identifying pre-established word commands from said audio-electrical signals and for generating corresponding identified electrical signals;
   computer means for generating operating electrical signals corresponding to said identified electrical signals;
   output signal generator means, responsive to said operating electrical signals to deliver actuating electrical signals to actuate said motor operated first means and to actuate said motor operated second means;
   whereby word commands corresponding to said pre-established word commands, applied to said sound detection means, will result in pre-established movements of said supporting structure and the focal length of said microscope.

8. The optical microscope of claim 7 wherein said pre-established word commands include two phrases which can be identified by said isolated-word recognition means, including:
   FOCUS UP, or its equivalent; and FOCUS DOWN, or its equivalent;
   and wherein said actuating electrical signal actuates said motor-operated second means to shorten or to lengthen the focal length of said microscope correspondingly.

9. In an optical microscope according to claim 7, memory means within said computer for pre-established words comprising:
UP; DOWN;
LEFT; RIGHT;
FORWARD; BACK;
ZOOM-UP; ZOOM-DOWN;
ZOOM FORWARD; ZOOM BACK;
ZOOM LEFT; ZOOM RIGHT;
FOCUS UP; FOCUS DOWN;
or the unique equivalent of each said pre-established word;
and wherein said activating electrical signals actuate said motor-operated first means to move said supporting structure respectively UP, DOWN, LEFT, RIGHT, FORWARD and BACK at a designated movement speed; and actuates said motor-operated second means to alter the focal length of said microscope.

10. In an optical microscope according to claim 7, memory means within said computer for pre-established words comprising:
UP; DOWN;
LEFT; RIGHT;
FORWARD; BACK;
ZOOM-UP; ZOOM-DOWN;
ZOOM FORWARD; ZOOM BACK;
ZOOM LEFT; ZOOM RIGHT;
FOCUS UP; FOCUS DOWN;
POINT; RETURN;
ONE; TWO; THREE; FOUR; FIVE;
or the unique equivalent of each said pre-established word;
and wherein said activating electrical signals, in response to one of said pre-established words, actuate said motor-operated first means to move said supporting structure respectively UP, DOWN, LEFT, RIGHT, FORWARD and BACK at a designated movement speed; and actuates said motor-operated second means to alter the focal length of said microscope; and wherein said activating electrical signals, in response to the POINT word command, actuate said motor-operated first means and said motor-operated second means to restore said microscope supporting structure and the said microscope focal length to a pre-established location and length corresponding to a location and length identified by the word command POINT, or its equivalent.

* * * * *